United States Patent
Oda et al.

(10) Patent No.: US 7,417,175 B2
(45) Date of Patent: Aug. 26, 2008

(54) INTERSTITIAL PROSTATISM MODEL ANIMAL

(75) Inventors: Nobuyuki Oda, Tokorozawa (JP); Kazuhisa Miyoshi, Hanno (JP); Akihiro Haruno, Tokorozawa (JP); Hidekazu Miyake, Tokushima (JP)

(73) Assignee: Taiho Pharmaceuticals Co., Ltd., Chiyoda-Ku, Tokyo (JP)

( * ) Notice: Subject to any disclaimer, the term of this patent is extended or adjusted under 35 U.S.C. 154(b) by 0 days.

(21) Appl. No.: 10/477,077

(22) PCT Filed: May 8, 2002

(86) PCT No.: PCT/JP02/04477

§ 371 (c)(1),
(2), (4) Date: Nov. 7, 2003

(87) PCT Pub. No.: WO02/089566

PCT Pub. Date: Nov. 14, 2002

(65) Prior Publication Data

US 2004/0139486 A1    Jul. 15, 2004

(30) Foreign Application Priority Data

May 9, 2001    (JP)    ............... 2001-138123

(51) Int. Cl.
*A01K 67/00*    (2006.01)
*A01K 67/027*    (2006.01)
(52) U.S. Cl. .................. 800/18; 800/8; 800/9
(58) Field of Classification Search ............ 800/3, 800/8, 21, 18
See application file for complete search history.

(56) References Cited

OTHER PUBLICATIONS

Gojo et al. (2000) Gene Therapy and Transplantation. Transplantation. 69:1995-1999.*
Chung et al. (1984) Tissue Interactions and Prostatic Growth. I. Induction of Adult Mouse Prostatic Hyperplasia by Fetal Urogenital Sinus Implants. 31:155-163.*
Goto et al. (2000) Gene Therapy and Transplantation. Transplantation. vol. 69, pp. 1995-1999.*
Jonathan P. Jarow and John T. Isaacs, "Prostatic Growth Effects of Rat Urogenital Sinus and Human Prostatic Tissue in the Rat," The Prostate 14, pp. 301-308, 1989.
Deland W.K. Chung, et al., "Tissue Interactions and Prostatic Growth: A New Mouse Model for Prostatic Hyperplasia," Annals New York Academy of Sciences, vol. 438, pp. 394-404, 1984.
Leland W.K. Chung and Gerald R. Cunha, "Stromal-Epithelial Interactions: II. Regulation of Prostatic Growth by Embryonic Urogenital Sinus Mesenchyme," The Prostate 4, pp. 503-511, 1983.
Yoshiki Sugimura, et al., "Regional Differences in the Inductive Activity of the Mesenchyme of the Embryonic Mouse Urogenital Sinus," The Prostate 7, pp. 253-260, 1985.
John E. McNeal, "Origin and Evolution of Benign Prostatic Enlargement," Investigative Urology, vol. 15, No. 4, pp. 340-345, 1978.
Thompson, T.C. (2000) "Mouse prostate reconstitution model system: a series of in vivo and in vitro models for benign and malignant prostatic disease" The Prostate 43:248-254.
Bostwick, D.G. (2000) "Prostatic intraepithelial neoplasia: animal models 2000" The Prostate 43:286-294.
Sharma, P. (1999) "Mouse models of prostate cancer" Oncogene 18:5349-5355.
Slawin, K. (1993) "Dietary fenretinide, a synthetic retinoid, decreases the tumor incidene and the tumor mass of ras+myc-induced carcinomas in the mouse prostate reconstitution model system" Cancer Research 53:4461-4465.
Supplementary Partial European Search Report from corresponding European patent application serial No. EP 02 76 9216.

* cited by examiner

*Primary Examiner*—Peter Paras, Jr.
*Assistant Examiner*—David A. Montanari
(74) *Attorney, Agent, or Firm*—Knobbe Martens Olson & Bear LLP

(57) ABSTRACT

The present invention provides an animal model for prostatic stromal hyperplasia, and a method for screening for a substance effective for preventing/treating human benign prostatic hyperplasia using the animal model. The animal model for prostatic stromal hyperplasia is produced by implanting the fetal urogenital sinus of a non-human animal under the skin or beneath the prostatic capsule of a non-human animal belonging to the species of the same as or different from the animal. A substance effective for preventing/treating human benign prostatic hyperplasia can be screened by administering a test substance to the animal model and measuring the preventive or therapeutic effect of the test substance upon the implanted tissue (fetal urogenital sinus or tissue derived therefrom).

3 Claims, 5 Drawing Sheets

Mean Value + Standard Error (8 subjects)

INTERSTITIAL PROSTATISM MODEL ANIMAL

This application is the U.S. National Phase under 35 U.S.C. §371 of International Application PCT/JP02/04477, filed on May 8, 2002, which claims priority of Japanese Patent Application No. 2001-138123, filed May 9, 2001. The International Application was published under PCT Article 21(2) in a language other than English.

TECHNICAL FIELD

The present invention relates to an animal model for prostatic stromal hyperplasia and a process for producing it. The invention also relates to a method for screening for a substance effective for preventing or treating human benign prostatic hyperplasia using such an animal model. The invention is further directed to a method for evaluating the preventive or therapeutic effect of each test substance on human benign prostatic hyperplasia.

BACKGROUND OF THE INVENTION

The prostate gland is a chestnut-shaped, hard mass of tissue located in the anteroinferior part of the male urinary bladder and between the urinary bladder and the urogenital diaphragm. The average weight of the adult prostate gland is about 20 grams. The urethra and a pair of ejaculatory ducts run through the center front of the prostate gland, thereby the prostate gland is anatomically divided into four lobes, When a man ages over 50, production of testosterone decreases and atrophic changes occur to the prostate gland, which performs secretory functions during a man's youth and middle age, and the functions thereof are decreased. From this time onwards, fibromuscular or glandular nodules appear on the glands around the urethra and gradually grow into large nodes. These nodes are benign tumors. The prostate gland with these nodes enlarges as a whole (60 to 100 g), this being called benign prostatic hyperplasia. The incidence of histologically enlarged prostate (enlarged nodes) increases with age. Prostatic hyperplasia is recognized in 50% of males over 60 years old, and about 90% of those over 85 years old.

Although the definition of benign prostatic hyperplasia (BPH) is not absolutely clear, it is understood as a disease that causes obstruction of the urethra due to the enlarged prostate gland. The subjective symptoms of benign prostatic hyperplasia are roughly divided into two types, i.e., obstructive symptoms such as urination difficulty, anuresis, prolonged urination, intermittent urination, and the like; and irritable symptoms such as frequent urination, urinary incontinence, nocturia, urinary urgency, and the like. The aforementioned obstructive symptoms is considered to be caused by two different mechanisms, i.e., organic obstruction in which enlarged prostate tumors press the urethra, and functional obstruction in which the prostatic capsule and stromal smooth muscles contract in response to sympathetic nerve stimulation. The functional obstruction is known to be caused by the stimulation of the sympathetic nervous system through α-receptors, and the therapeutic effect of such functional obstruction has recently been increased due to the development of α-blockers. However, the specific mechanism inducing organic obstruction has not yet been revealed, and no effective therapeutic agents have been developed. Therefore, the immediate development of such therapeutic agents is desired.

The prostate tissue primarily consists of epithelial and stromal components. In human benign prostatic hyperplasia in which organic disorders are caused by the enlargement of the prostate tissue, it has been reported that stromal enlargement resulting from the increase of stromal components is frequently observed as a morphologic feature. The increase of epithelial components is known to result primarily from the growth of hormone-sensitive epithelial cells, and as a therapeutic agent anti-hormonal agents are used. However, no pharmaceuticals that can specifically inhibit the above-described stromal enlargement that is frequently observed in humans are known. Therefore, demand exists for pharmaceuticals that have activity to specifically inhibit or improve such prostatic stromal hyperplasia.

Incidentally, for developing or evaluating pharmaceuticals, it is known that using an animal model that reflects specific human pathological condition instead of using a normal animal, when screening medicinal ingredients or evaluating pharmacological actions of various substances provides results closer to actual clinical data.

DISCLOSURE OF THE INVENTION

The present invention provides a non-human animal pathological model effective for use in developing pharmaceuticals for preventing or treating human benign prostatic hyperplasia. In particular, the invention provides a non-human animal pathological model for prostatic hyperplasia, having enlarged stromal tissue as specifically observed in a human benign prostatic hyperplasia patient. Moreover, the invention provides a method for producing a non-human animal pathological model for prostatic hyperplasia, having enlarged stromal tissue as specifically observed in a human benign prostatic hyperplasia patient.

Furthermore, the present invention provides a method for screening for a pharmaceutical effective for preventing or treating human benign prostatic hyperplasia, and a method for evaluating the medicinal effects of each test substance on preventing or treating human benign prostatic hyperplasia.

It is known that the urogenital sinus is the anlage of the prostate gland formed at the front part of the endodermal cloaca during the fetal period. In the fetal period, a prostate epithelial blast cell appeared at the stroma of the posterior wall of the urogenital sinus. This blast cell differentiates and proliferates into the matured prostate. In addition, McNeal et al., presume that the trait of tissue and cells during the fetal period in which cells actively divide is similar to that of pathological tissues in which cells excessively proliferate (McNeal J E: Origin and evolution of benign prostatic enlargement. Invest. Urol. 15: 340-345, 1978; McNeal J E: Anatomy of the prostate and morphogenesis of benign prostatic hyperplasia). Moreover, Cunha et al., to histologically and physiologically investigate the prostate gland, implanted embryonic urogenital sinus into the prostate gland or beneath the renal capsule using a mouse and a rat, and reported the results of various research conducted on the matured prostate gland formed at least 4 weeks after Implantation (Chung L W K, Cunha G R: Stromal-Epithelial Interactions: II. Regulation of prostatic growth by embryonic urogenital sinus mesenchyme. The Prostate 4: 503-511, 1983). However, the matured prostate glands derived from the mouse and rat obtained by the above-described method exhibited epithelial-dominant tissue structures, which are different from the stroma-dominant tissue structures observed in human benign prostatic hyperplasia.

On the bases of these prior findings, the inventors conducted extensive research to produce an animal model having stroma-dominant, prostate-like tissue that can reflect human benign prostatic hyperplasia. The inventors then found that, by subcutaneously implanting the urogenital sinus of a fetus (20 or 21 day-old) of a non-human animal (donor) into a non-human animal (recipient), the implanted fetal urogenital sinus differentiates and develops under the skin to form stroma-dominant tissue, as specifically observed in human benign prostatic hyperplasia patients.

Furthermore, the inventors found that, by implanting a fetal urogenital sinus beneath the prostatic capsule of a non-human animal (recipient), the implanted fetal urogenital sinus differentiates and develops beneath the prostatic capsule to form stroma-dominant tissue as specifically observed in human hyperplasia patients.

As described above, in human benign prostatic hyperplasia, stromal enlargement, which is caused by the increase in stromal components, is specifically observed. Therefore, the stroma-dominant tissue formed under the skin or beneath the prostatic capsule by implanting a fetal urogenital sinus, which is a prostate gland-anlage cellular structure, is prostate-like tissue reflecting human benign prostatic hyperplasia.

On the basis of these findings, non-human animals having such tissue as described above are useful as animal pathological models for human benign prostatic hyperplasia. The use of such animal models enables pharmaceuticals effective for preventing or treating human benign prostatic hyperplasia to be obtained, and enables the preventive or therapeutic effects of various substances with respect to human benign prostatic hyperplasia to be evaluated. The present invention was accomplished based on such findings.

In particular, the invention relates to animal models of prostatic stromal hyperplasia described in Items A and B below:

A. A non-human animal model for prostatic stromal hyperplasia having an extraneous fetal urogenital sinus or tissue derived therefrom under the skin.

Embodiments of such a non-human animal model of prostatic stromal hyperplasia include the following:

A-1. A non-human animal model for prostatic stromal hyperplasia according to Item (A), wherein subcutaneous refers to abdominal subcutaneous.

A-2. A non-human animal model for prostatic stromal hyperplasia according to Item (A) or (A-1), wherein the fetal urogenital sinus is donated from an animal belonging to the species of the same as or different from the non-human animal model for prostatic stromal hyperplasia.

A-3. A non-human animal model for prostatic stromal hyperplasia according to any of Items (A) to (A-2) produced by subcutaneously implanting the fetal urogenital sinus of a non-human animal into a non-human animal belonging to the species of the same as or different from the said animal.

A-4. A non-human animal model for prostatic stromal hyperplasia according to any of Items (A) to (A-3), wherein the animal donating the fetal urogenital sinus or the non-human animal model for prostatic stromal hyperplasia is, the same or different, a non-human animal selected from a mouse, a nude mouse, a rat, and a nude rat.

A-5. A non-human animal model for prostatic stromal hyperplasia according to any of Items (A) to (A-4), wherein the animal donating the fetal urogenital sinus is a mouse or rat, and the non-human animal model for prostatic stromal hyperplasia is, the same or different, a non-human animal selected from a mouse, a nude mouse, a rat, and a nude rat.

The non-human animal model for prostatic stromal hyperplasia described above is animal pathological model having under the skin stromal-dominant tissue as specifically observed in benign prostatic hyperplasia patients.

B. A non-human animal model for prostatic stromal hyperplasia having an extraneous fetal urogenital sinus or tissue derived therefrom beneath the prostatic capsule.

Embodiments of such a non-human animal model for prostatic stromal hyperplasia include the following:

B-1. A non-human animal model for prostatic stromal hyperplasia according to Item (B), wherein the fetal urogenital sinus is donated from an animal belonging to the species of the same as or different from the non-human animal model for prostatic stromal hyperplasia.

B-2. A non-human animal model for prostatic stromal hyperplasia according to Item (B) to (B-1) produced by implanting the fetal urogenital sinus of a non-human animal beneath the prostatic capsule of a non-human animal belonging to the species of the same as or different from the said animal.

B-3. A non-human animal model for prostatic stromal hyperplasia according to any of Items (B) to (B-2), wherein the animal donating the fetal urogenital sinus or the non-human animal model for prostatic stromal hyperplasia is, the same or different, a non-human animal selected from a mouse, a nude mouse, a rat, and a nude rat.

B-4. A non-human animal model for prostatic stromal hyperplasia according to any of Items (B) to (B-3), wherein the animal donating the fetal urogenital sinus is a mouse or rat, and the non-human animal model for prostatic stromal hyperplasia is, the same or different, a non-human animal selected from a mouse, a nude mouse, a rat, and a nude rat.

The non-human animal model for prostatic stromal hyperplasia described above is animal pathological model reflecting more closely the pathogenic conditions of human benign prostatic hyperplasia by having beneath the prostatic capsule stroma-dominant tissue as specifically observed in a benign prostatic hyperplasia patient.

Furthermore, the present invention is directed to methods for producing animal models for prostatic stromal hyperplasia as described in Items C and D below. The non-human animal model for prostatic stromal hyperplasia described in Item A can be produced according to the method described in Item C below. The non-human animal model for prostatic stromal hyperplasia described in Item B can be produced according to the method described in Item D below.

C. A method for producing a non-human animal model for prostatic stromal hyperplasia comprising the steps of:

(i) subcutaneously implanting a fetal urogenital sinus of a non-human animal into a non-human animal belonging to the species of the same as or different from the said animal, and (ii) forming stroma-enlarged tissue under the skin by rearing the urogenital sinus-implanted non-human animal, as required.

Embodiments of the said method for producing a non-human animal model for prostatic stromal hyperplasia include the following:

C-1. A method for producing a non-human animal model for prostatic stromal hyperplasia according to Item (C), wherein a subcutaneous site where the fetal urogenital sinus is implanted is an abdominal subcutaneous site.

C-2. A method for producing a non-human animal model for prostatic stromal hyperplasia according to Item (C) or (C-1), wherein step (i) comprises subcutaneously implanting the fetal urogenital sinus of a rat into a nude mouse.

D. A method for producing a non-human animal model for prostatic stromal hyperplasia comprising the steps of:

(i) implanting a fetal urogenital sinus of a non-human animal beneath the prostatic capsule of a non-human animal belonging to the species of the same as or different from the said animal, and (ii) forming stroma-enlarged tissue beneath the prostatic capsule by rearing the urogenital sinus-implanted non-human animal, as required.

Embodiments of the method for producing a non-human animal model for prostatic stromal hyperplasia include the following:

D-1. A method for producing a non-human animal model for prostatic stromal hyperplasia according to Item (D), wherein step (i) comprises implanting the fetal urogenital sinus of a non-human animal beneath the prostatic capsule of a non-human animal belonging to the same species as a non-human animal donating the fetal urogenital sinus.

D-2. A method for producing a non-human animal model for prostatic stromal hyperplasia according to Item (D) or (D-1), wherein step (i) comprises implanting the fetal urogenital sinus of a rat beneath the prostatic capsule of a rat.

In the production methods described in Items C and D above, non-human animal models for prostatic stromal hyperplasia prepared in step (i) can be effectively used in methods described herein below for screening for a substance effective for preventing human prostatic stromal hyperplasia, and for evaluating the preventive effect of a test substance on human prostatic stromal hyperplasia.

Furthermore, in the production methods described in Items C and D above, non-human animal models for prostatic stromal hyperplasia prepared by steps (i) and (ii) can be effectively used in methods that will be described later for screening for a substance effective for treating human prostatic stromal hyperplasia, and for evaluating the therapeutic effect of a test substance on human prostatic stromal hyperplasia.

Moreover, the present invention is directed to a method for screening for a substance effective for preventing or treating human benign prostatic hyperplasia as described in Item E below:

E. A method for screening for a substance effective for preventing or treating human benign prostatic hyperplasia comprising:
administering a test substance to the non-human animal model for prostatic stromal hyperplasia of Item (A) or (B) above, and
measuring the preventive or therapeutic effect of the test substance on the extraneous fetal urogenital sinus or tissue derived therefrom of the animal model.

The term "the extraneous fetal urogenital sinus or tissue derived therefrom" as used herein refers to the fetal urogenital sinus immediately after implantation into an animal or in an early stage of rearing the animal, as well as to the tissue (fetal urogenital sinus-derived tissue) formed from the fetal urogenital sinus after a certain period of time after implantation. In the present invention, "the extraneous fetal urogenital sinus and tissue derived therefrom" is sometimes simply called "the implanted tissue". Furthermore, the term "extraneous fetal urogenital sinus" is sometimes simply called "fetal urogenital sinus", and the term "tissue derived from the extraneous fetal urogenital sinus" is sometimes simply called "fetal urogenital sinus-derived tissue".

In Item E above, the non-human animal model for prostatic stromal hyperplasia of Item (A) or (B) includes their respective specific embodiments, i.e., the non-human animal models for prostatic stromal hyperplasia disclosed in Items (A-1) to (A-5) and Items (B-1) to (B-4).

The screening method described in Item E includes the following embodiments:

E-1-1. A method for screening for a substance effective for treating human benign prostatic hyperplasia comprising steps (a) to (c) below:
(a) administering a test substance to at least one of the non-human animal models for prostatic stromal hyperplasia of Items (A) and (B), and rearing it;
(b) measuring the stromal area ratio or weight of the implanted tissue of the non-human animal model for prostatic stromal hyperplasia; and
(c) selecting a test substance that reduces the stromal area ratio or weight based on the result obtained in (b) in comparison with the stromal area ratio or weight of the implanted tissue of the non-human animal model for prostatic stromal hyperplasia before administering the test substance.

E-1-2. A method for screening for a substance effective for treating human benign prostatic hyperplasia according to Item (E-1-1) comprising:
conducting the screening including steps (a) to (c) using the non-human animal model for prostatic stromal hyperplasia of Item (A), and
conducting, on the test substance selected by the above screening, the screening including steps (a) to (c) using the non-human animal model for prostatic stromal hyperplasia of Item (B).

E-1-3. A method for screening for a substance effective for treating human benign prostatic hyperplasia according to Item (E-1-1) or (E-1-2) using a non-human animal model for prostatic stromal hyperplasia produced according to a method including steps (i) and (ii) recited in Item (C) or (D) as the non-human animal model for prostatic stromal hyperplasia of Item (A) or (B).

E-2-1. A method for screening for a substance effective for preventing human benign prostatic hyperplasia comprising steps (a) to (c) below:
(a) administering a test substance to at least one of the non-human animal models for prostatic stromal hyperplasia of Item (A) and (B), and rearing it;
(b) measuring the stromal area ratio or weight of the implanted tissue of the non-human animal model for prostatic stromal hyperplasia; and
(c) selecting a test substance that inhibits the increase of the stromal area ratio or weight based on the result obtained in (b) in comparison with the stromal area ratio or weight of the implanted tissue of a corresponding control non-human animal model for prostatic stromal hyperplasia that is not administered with the test substance.

E-2-2. A method for screening for a substance effective for preventing human benign prostatic hyperplasia according to Item (E-2-1) comprising:
conducting the screening including steps (a) to (c) using the non-human animal model for prostatic stromal hyperplasia of Item (A), and
conducting, on the test substance selected by the above screening, the screening including steps (a) to (c) using the non-human animal model for prostatic stromal hyperplasia of Item (B).

E-2-3. A method for screening for a substance effective for preventing human benign prostatic hyperplasia according to Item (E-2-1) or (E-2-2), using a non-human animal model for prostatic stromal hyperplasia produced according to a method including step (i) but step (ii) recited in Item (C) or (D) as the non-human animal model for prostatic stromal hyperplasia of Item (A) or (B).

Furthermore, the present invention is directed to a pharmaceutical composition for preventing or treating human benign prostatic hyperplasia as described in Item F below:

F. A pharmaceutical composition for preventing or treating human benign prostatic hyperplasia comprising as an active ingredient a substance selected according to the screening method of Item (E).

Such a pharmaceutical composition includes the following embodiments:

F-1-1. A pharmaceutical composition for treating human benign prostatic hyperplasia comprising as an active ingredient a substance selected according to the screening method disclosed in any of Items (E-1-1) to (E-1-3).

F-1-2. A pharmaceutical composition for treating human benign prostatic hyperplasia comprising a substance selected according to the screening method disclosed in any of Items (E-1-1) to (E-1-3) in an amount effective for treating human benign prostatic hyperplasia, and a pharmaceutically acceptable carrier or additive.

F-1-3. Use of a substance selected according to the screening method disclosed in any of Items (E-1-1) to (E-1-3) for producing a pharmaceutical composition for treating human benign prostatic hyperplasia.

F-2-1. A pharmaceutical composition for preventing human benign prostatic hyperplasia comprising as an active ingredient a substance selected according to the screening method disclosed in any of Items (E-2-1) to (E-2-3).

F-2-2. A pharmaceutical composition for preventing human benign prostatic hyperplasia comprising a substance selected according to the screening method disclosed in any of Items (E-2-1) to (E-2-3) in an amount effective for preventing human benign prostatic hyperplasia, and a pharmaceutically acceptable carrier or additive.

E-2-3. Use of a substance selected according to the screening method disclosed in any of Items (E-2-1) to (E-2-3) for producing a pharmaceutical composition for preventing human benign prostatic hyperplasia.

Moreover, the present invention relates to a method for evaluating the preventive or therapeutic effect of a test substance on human benign prostatic hyperplasia as described in Item G below;

G. A method for evaluating the preventive or therapeutic effect of a test substance on human benign prostatic hyperplasia comprising:

administering a test substance to at least one of the non-human animal models for prostatic stromal hyperplasia of Items (A) and (B), and measuring the preventive or therapeutic effect of the test substance administered on an extraneous fetal urogenital sinus or tissue derived therefrom (implanted tissue).

In particular, in the method above, the preventive effect or therapeutic effect of a test substance administered on an extraneous fetal urogenital sinus or tissue derived therefrom (implanted tissue) can be evaluated by measuring the change in the configuration, specifically stromal area ratio, or in the weight, of the extraneous fetal urogenital sinus or tissue derived therefrom (implanted tissue).

The non-human animal model for prostatic stromal hyperplasia of Item (A) or (B) used above includes their respective specific embodiments, i.e., the non-human animal models for prostatic stromal hyperplasia disclosed in Items (A-1) to (A-5) and Items (B-1) to (B-4).

Such an evaluation method includes the following embodiments:

G-1-1. A method for evaluating the therapeutic effect of a test substance on human benign prostatic hyperplasia comprising steps (a) and (b) below:

(a) administering a test substance to at least one of the non-human animal models for prostatic stromal hyperplasia of Items (A) and (B), and rearing it; and (b) comparing the stromal area ratio or weight of the implanted tissue of the non-human animal model for prostatic stromal hyperplasia with the stromal area ratio or weight of the implanted tissue of the non-human animal model for prostatic stromal hyperplasia before administering the test substance.

G-1-2. A method for evaluating the therapeutic effect of a test substance on human benign prostatic hyperplasia according to Item (G-1-1) further comprising step (c):

(c) evaluating the therapeutic effect of the test substance on human benign prostatic hyperplasia using any reduction in the stromal area ratio or weight of the implanted tissue as an indicator, based on the result of the comparison in step (b).

G-1-3. A method for evaluating the therapeutic effect on human benign prostatic hyperplasia according to Item (G-1-1) or (G-1-2) comprising:

conducting the evaluation method comprising the aforementioned steps (a) and (b) and optionally (c) using the non-human animal model for prostatic stromal hyperplasia of Item (A); and further conducting, on the test substance selected from test substances subjected to the above evaluation method, the evaluation method comprising the aforementioned steps (a) and (b) and optionally (c) using the non-human animal model for prostatic stromal hyperplasia of Item (B).

G-1-4. A method for evaluating the therapeutic effect on human benign prostatic hyperplasia according to any of Items (G-1-1) to (G-1-3) using a non-human animal model for prostatic stromal hyperplasia produced according to a method including steps (i) and (ii) recited in Item (C) or (D) as the non-human animal model for prostatic stromal hyperplasia of Item (A) or (B).

G-2-1. A method for evaluating the preventive effect of a test substance on human benign prostatic hyperplasia comprising steps (a) and (b) below:

(a) administering a test substance to at least one of the non-human animal models for prostatic stromal hyperplasia of Item (A) and (B), and rearing it; and (b) comparing the stromal area ratio or weight of the implanted tissue for the non-human animal model of prostatic stromal hyperplasia With the stromal area ratio or weight of the implanted tissue of a corresponding control animal model for prostatic stromal hyperplasia that is not administered with the test substance.

G-2-2. A method for evaluating the preventive effect on human benign prostatic hyperplasia according to Item (G-2-1) further comprising step (c):

(c) evaluating the preventive effect of the test substance on human benign prostatic hyperplasia, using any suppression of increase of the stromal area ratio or weight of the implanted tissue as an indicator, based on the result of the comparison in step (b).

G-2-3. A method for evaluating the preventive effect on human benign prostatic hyperplasia according to Item (G-2-1) or (G-2-2) comprising:

conducting the evaluation method comprising the aforementioned steps (a) and (b) and optionally (c) using the non-human animal model for prostatic stromal hyperplasia of Item (A); and further conducting, on the test substance selected from test substances subjected to the above evaluation, the evaluation method comprising the aforementioned steps (a) and (b) and optionally (c) using the non-human animal model for prostatic stromal hyperplasia of Item (B).

G-2-4. A method for evaluating the preventive effect on human benign prostatic hyperplasia according to any of Items (G-2-1) to (G-2-3) using a non-human animal model for prostatic stromal hyperplasia produced according to a method including step (i) but step (ii) recited in Item (C) or (D) as the non-human animal model for prostatic stromal hyperplasia of Item (A) or (B).

Figure 1:
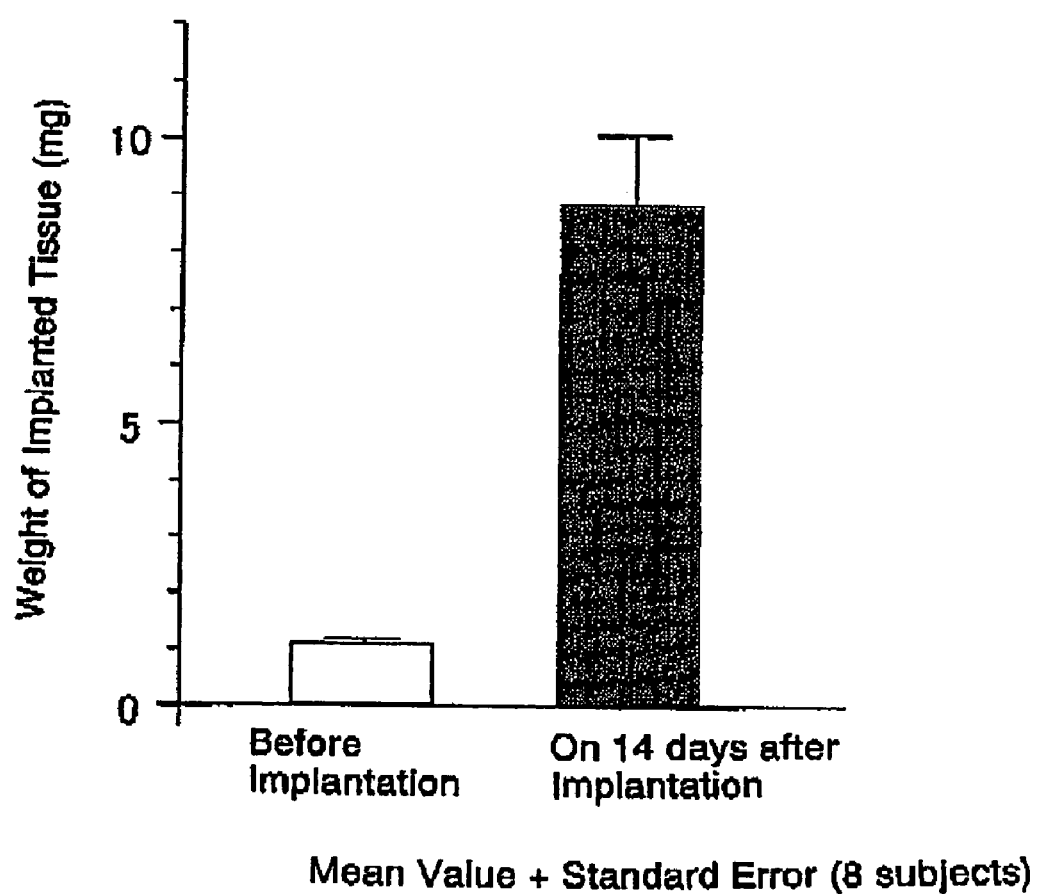
FIG. 1 shows a comparison of the weight (mg) of tissue (rat urogenital sinus or tissue derived from rat urogenital sinus: shown as "Implanted Tissue" in the figure) subcutaneously implanted into nude mice between before implantation and on 14 days after implantation (Example 1 (3)).

BEST MODE FOR CARRYING OUT THE INVENTION (1) Non-human Animal Models for Prostatic Stromal Hyperplasia and Methods for Their Production.

The non-human animal model for prostatic stromal hyperplasia of the present invention refers to animals other than humans, having stroma-dominant tissue as specifically observed in the prostate tissue of human benign prostatic hyperplasia patients. The phrase "having stroma-dominant tissue" collectively refers to both of the cases in having stroma-dominant tissue as a practical matter and cases in having stroma-dominant tissue with implications (in other words, animals possess a possibility of developing stroma-dominant tissue in the future).

The animal models of the invention can be largely divided into an animal model (i) that has stroma-dominant tissue under the skin, and an animal model (ii) that has stroma-dominant tissue beneath the prostatic capsule. The latter animal model (ii) substantially has prostate-like tissue exhibiting a stroma-dominant tissue, and can be considered as an animal pathological model directly reflecting human benign prostatic hyperplasia.

Specifically, the animal model (i) of the invention has an extraneous fetal urogenital sinus or fetal urogenital sinus-derived tissue formed therefrom under the skin, while the animal model (ii) of the invention has an extraneous fetal urogenital sinus or fetal urogenital sinus-derived tissue formed therefrom beneath the prostatic capsule. The term "extraneous" herein refers to being derived from non-self. In particular, animal models having an extraneous fetal urogenital sinus or tissue derived therefrom mean animal models having a fetal urogenital sinus originating from a different individual or fetal urogenital sinus-derived tissue formed therefrom regardless of the animal species.

Examples of animals for use in producing such animal models include, for both donor animal that provides the fetal urogenital sinus and recipient animal that is implanted with the donated fetal urogenital sinus, non-human mammals that are generally used in experiments, such as rats, nude rats, mice, nude mice, guinea pigs, hamsters, rabbits, dogs, and monkeys. Preferable are rodents such as rats, nude rats, mice, nude mice, guinea pigs, hamsters, rabbits, etc. More preferable, for ease of operation and rearing, are rats, nude rats, mice, and nude mice.

Donor animal and recipient animal can be of the same or different species. Although it is preferred that donor animal and recipient animal are of the same species each other from the immunological view point, when an immunodeficient animal such as a nude mouse, a nude rat, etc., is used as a recipient, animal of different species can be used as a donor.

Preferable examples of donor animals are rats and mice. Preferable examples of recipient animals are mice, nude mice, rats, and nude rats.

The respective production methods for animal models (i) and (ii) above will be described below:

(i) Animal Model Having a Fetal Urogenital Sinus or Fetal Urogenital Sinus-derived Tissue Under the Skin Such an animal model can be produced by implanting the fetal urogenital sinus of a donor animal under the skin of a recipient animal.

In practice, donor animal is a pregnant female with fetus because it donates fetal urogenital sinus. The fetal urogenital sinus to be implanted into a recipient animal can be removed and collected from the fetus of the donor animal. Although such fetuse is not limited, when a rat is used, 18- to 21-day-old fetuse is preferable for use. The fetal age can be selected according to the type of recipient animal into which the fetal urogenital sinus is implanted. For example, when recipient is a rat, 20-day-old fetuse is preferable. When recipient is a nude mouse, 21-day-old fetuse is preferable.

Furthermore, when recipient animal is a rat, mouse, nude mouse, nude rat, etc., for example, 5- to 8-week-old recipient animal is preferable for use.

Specifically, the animal model of the present invention can be produced according to the method described below. First, the urogenital sinus removed from the fetus of a donor animal is subcutaneously implanted into a recipient animal. A subcutaneous site requires a simple implantation procedure and therefore is a preferable implantation site. When subcutaneous implantation is conducted, although not limited, it is performed under the abdominal skin for high graft survival (about 80% or more) of the implanted urogenital sinus. Subcutaneous implantation, especially abdominal subcutaneous implantation, is preferably conducted, although also not limited to, using a nude mouse as a recipient animal. The implantation operation of the urogenital sinus is not limited and can be performed according to standard implantation procedures.

The animal model of the invention is produced by implanting the fetal urogenital sinus provided by a donor animal under the skin of a recipient animal and suturing the implantation site. The animal model of the invention after implantation may be reared under normal or aseptic conditions as required. Rearing conditions are not limited, and examples of specific conditions are temperature: 20 to 26° C.; humidity: 30 to 70%; feeding/watering: ad libitum; and lighting: 12-hour light-dark cycle.

The rearing period after implantation is, but not limited to, preferably 12 days or more, more preferably 14 days or more, for any of a rat, a mouse, a nude rat, and a nude mouse. More specifically, the preferable rearing period for a rat or nude rat is 14 days or more, and more preferably 21 days or more. The preferable rearing period for a mouse or nude mouse is 12 days or more, and especially 14 days or more.

By rearing the implanted animal for a certain period, the subcutaneously implanted urogenital sinus differentiates and develops at the implantation site into tissue having stroma-dominant, prostate-like histological characteristics. Specifically, as evidenced in Examples below, by rearing nude mice for 14 days or more, the weight of implanted tissue (fetal urogenital sinus-derived tissue) increased nearly 9 to 10 times, and the stromal component accounted for 70% or more of the implanted tissues. In the implanted tissue (fetal urogenital sinus-derived tissue), secreted substances were observed in the lumen composed of epithelial cells, showing that the implanted tissue differentiated to a tissue having a secretory function equivalent to the prostate tissue. As described above, the animal model of the invention produced by rearing for a certain period after fetal urogenital sinus implantation has tissue exhibiting stroma-dominant characteristics under the skin that is similar to the prostate tissue of human benign prostatic hyperplastic patients, and thereby can be provided as an animal pathological model for human benign prostatic hyperplasia.

(ii) Animal Model Having a Fetal Urogenital Sinus or Fetal Urogenital Sinus-Derived Tissue Beneath the Prostatic Capsule Such an animal model can be produced by implanting the fetal urogenital sinus of a donor animal beneath the prostatic capsule of a recipient animal.

Donor animals used herein, methods for removing fetuses and fetal urogenital sinuses from donor animals, fetal ages, and recipient animals are identical to those described in (i) above.

Specifically, the animal model of the present invention can be produced according to the method described below. First, the urogenital sinus removed from the fetus of a donor animal is implanted beneath the prostatic capsule of a recipient animal. A site beneath the prostatic capsule is a preferable implantation site because the environment of the implanted urogenital sinus is physiologically close to the environment the prostate gland is located in, and an animal model having stroma-enlarged, prostate-like tissue that exhibits the desired pathological state of prostatic hyperplasia can be obtained. Implantation beneath the prostatic capsule is preferably conducted, without being limited, to using a rat as a recipient animal. The implanting operation of the urogenital sinus is not restricted and can be performed according to standard implantation procedures.

The animal model of the invention is produced by implanting the fetal urogenital sinus provided by a donor animal beneath the prostatic capsule of a recipient animal and suturing the implantation site. The animal model of the invention after implantation may be reared under normal or aseptic conditions as required. Rearing conditions are not limited, and examples of specific conditions are temperature: 20 to 26° C.; humidity: 30 to 70%; feeding/watering: ad libitum; and lighting: 12-hour light-dark cycle.

The rearing period after implantation is, but not be limited to, as with the animal model described in (i) above, 12 days or more, preferably for 14 days or more, for any of a rat, a nude rat, a mouse, and a nude mouse. More specifically, the preferable rearing period for a rat or nude rat is 14 days or more, especially 21 days or more. The preferable rearing period for a mouse or nude mouse is 12 days or more, especially 14 days or more.

By rearing the implanted animal for a certain period, the urogenital sinus implanted beneath the prostatic capsule differentiates and develops into tissue having stroma-dormant, prostate gland-like histological characteristics. Specifically, as evidenced in the Examples below, by rearing rats for 21 days or more after implantation, the weight of implanted tissue (fetal urogenital sinus-derived tissue) significantly increased, and the stromal component accounted for 70% or more of the implanted tissue. In the implanted tissue (fetal urogenital sinus-derived tissue), secreted substances were observed in the lumen composed of epithelial cells, showing that the implanted tissue differentiated to a tissue having a secretory function equivalent to the prostate tissue. As described earlier, the animal model of the invention produced by rearing for a certain period after fetal urogenital sinus implantation beneath the prostatic capsule has tissue exhibiting stroma-dominant characteristics similar to the prostate tissue of human benign prostatic hyperplasia patients, and thereby can be provided as an animal pathological model for human benign prostatic hyperplasia.

Animal models (i) and (ii) of the present invention broadly include non-human animals implanted with a fetal urogenital sinus regardless of the presence or absence of rearing period after fetal urogenital sinus implantation, or the length of the rearing period. Specifically, animal model for prostatic hyperplasia (i) refers to an animal having stroma-dominant, prostate-like tissue under the skin similar to the tissue of a human benign prostatic hyperplasia patient or an animal that is likely to develop such tissue in the future. The other embodiment, i.e., animal model for prostatic hyperplasia (ii), includes an animal pathological model having beneath the prostatic capsule the stroma-dominant prostate gland reflecting prostatic hyperplasia or an animal model that may develop such a pathological condition in the future.

Animal models (i) and (ii) can both be effectively used in evaluating/determining the medicinal properties of pharmaceuticals (test substances) that are expected to have a preventive or therapeutic effect on human benign prostatic hyperplasia, especially that caused by stromal enlargement, and can be effectively used in screening for active substances that have a preventive or therapeutic effect on human benign prostatic hyperplasia.

In this case, according to the period of rearing after implanting the fetal urogenital sinus (i.e., according to the proliferation or differentiation/development of the implanted tissue), the purpose of screening (whether screening for substances effective for remedy or for substances effective for prevention) or the purpose of evaluation (whether evaluating a therapeutic effect or a preventive effect) can be suitably selected.

Specifically, animal models (i) and (ii), which are produced by implanting a fetal urogenital sinus under the skin or beneath the prostatic capsule, and then without rearing or rearing for a short period (desirably, less than 14 days, preferably less than 12 days in case of a nude mouse; less than 21 days, preferably less than 14 days in case of a rat), can be effectively used in searching for substances effective for preventing human benign prostatic hyperplasia and in evaluating the preventive effects of test substances on human benign prostatic hyperplasia. Furthermore, animal models (i) and (ii) produced by implanting a fetal urogenital sinus under the skin or beneath the prostatic capsule, and then rearing for a certain period (desirably, for 12 days or more, and preferably for 14 days or more in case of a nude mouse; for 14 days or more, preferably for 21 days or more in case of a rat), can be effectively used in searching for substances effective for treating human benign prostatic hyperplasia and in evaluating the therapeutic effect of each test substance on human benign prostatic hyperplasia.

(2) Method for Screening for a Substance Effective for Preventing/Treating Human Benign Prostatic Hyperplasia The present invention is directed to a method using the animal model of the above-mentioned present invention for screening for a substance effective for preventing or treating the benign prostatic hyperplasia caused especially by stromal enlargement.

Specifically, the method can be practiced by administering a test substance to the non-human animal model for prostatic stromal hyperplasia (i) or (ii), and measuring the preventive or therapeutic effect of the test substance on the implanted tissue (fetal urogenital sinus or fetal urogenital sinus-derived tissue) of the animal model.

Test substances usable herein are not limited and examples thereof include low-molecular-weight organic/inorganic compounds, high-molecular-weight organic/inorganic compounds, nucleic acids, amino acids, peptides, and proteins. These substances can be in purified form, or in crudely purified form such as extracts obtained from plants, animals, microorganisms, etc. Moreover, methods for producing test substances are not limited. Test substances can be those that are isolated from natural materials, chemically or biochemically synthesized, and genetically engineered.

Methods for administering the test substance to the non-human animal model for prostatic stromal hyperplasia are also not limited. According to the type of test substance, oral administration or parenteral administration such as subcutaneous, intravenous, topical, percutaneous, or enteral administration can suitably be selected. Oral administration is preferable regardless of the animal models of both (i) and (ii).

(2-1) Screening for a Substance Effective for Preventing Human Benign Prostatic Hyperplasia Screening for a substance effective for preventing benign prostatic hyperplasia can be practiced by administering a test substance to the non-human animal model for prostatic stromal hyperplasia (i) or (ii), rearing the animal model for a certain period, measuring the weight and histologic properties (stromal component ratio and the like) of the implanted tissue (fetal urogenital sinus-derived tissue) of the animal model, and evaluating the test substance.

As the non-human animal model for prostatic stromal hyperplasia (i) or (ii) used in screening for a preventive substance, among the non-human animal models for prostatic stromal hyperplasia described above, animal model (i) or (ii) is used, which is produced by without rearing or rearing a short period after implanting a fetal urogenital sinus under the skin or beneath the prostatic capsule. Desirably, when a mouse or nude mouse is used, this animal model is used either immediately after implanting the fetal urogenital sinus, or within 14 days of rearing after implantation, and preferably within 12 days. When a rat or nude rat is used, this animal model is used either immediately after implanting the fetal urogenital sinus, or within 21 days of rearing after the implantation and preferably within 14 days.

A method for administering a test substance into the non-human animal model for prostatic stromal hyperplasia (i) or (ii) is as described above. The non-human animal model for prostatic stromal hyperplasia (i) or (ii) administered with a test substance is reared for a certain period. Rearing conditions are not limited, and normal conditions and aseptic conditions can be employed as necessary. Examples of specific conditions are, although not limited to, temperature: 20 to 26° C.; humidity: 30 to 70%; feeding/watering: ad libitum; and lighting: 12-hour light-dark cycle.

In this case, the rearing period after implantation is not limited, but desirable rearing period is 12 days or more, and preferably 14 days or more, for a rat, a mouse, a nude rat, or a nude mouse. More specifically, 14 days or more of rearing period is desirable for a rat or nude rat, especially 21 days or more. For a mouse or nude mouse, 12 days or more of rearing period is desirable, especially 14 days or more.

After rearing, the test substance can be evaluated, after removing the implanted tissue (the fetal urogenital sinus-derived tissue) of the animal model, by measuring the weight of the implanted tissue or examining the histological properties of the implanted tissue. Specifically, the test substance can be evaluated by measuring the weight of the implanted tissue (fetal urogenital sinus-derived tissue), and examining its influence on the weight increase, as specifically observed in the prostate tissue affected by human benign prostatic hyperplasia, or examining its influence on the increase of the proportion of the stromal component (stromal area ratio), as specifically observed in prostate tissue affected by human benign prostatic hyperplasia. The proportion of the stromal component in tissue (stromal area ratio) can be calculated using, for example, keratin staining, hematoxylin-eosin staining, and the like, although it is not limited to these methods.

More specifically, the evaluation of the test substance can be conducted as follows: A control non-human animal model for prostatic stromal hyperplasia administered with no test substances is reared in the same manner; the weight or the proportion of the stromal component (stromal area ratio) of the implanted tissue (fetal urogenital sinus-derived tissue) is measured; and the weight or the proportion of the stromal component (or extent of its increase) of the implanted tissue of the test animal administered with a test substance and the weight or the proportion of the stromal component of the implanted tissue of the aforementioned control animal are compared. In this case, a test substance that decreases the weight of the implanted tissue (fetal urogenital sinus-derived tissue) or the proportion of the stromal component (or the extent of its increase) of the implanted tissue of the test animal when compared with that of the control animal is identified as a substance that inhibits or alleviates the prostate tissue enlargement, i.e., an active substance having a preventive effect on human benign prostatic hyperplasia.

Such a substance effective for prevention can be screened using as a test subject the non-human animal model for prostatic stromal hyperplasia either (i) or (ii). The screening method using the non-human animal model for prostatic stromal hyperplasia (i) provides the advantage of enabling the test substance to be screened for by using a small amount of the test substance and a simple operation, and the advantage of enabling the medicinal properties of the test substance to be evaluated in a short period (about 2 weeks) because of the use of the animal model produced by subcutaneous implantation. On the other hand, the screening method using the non-human animal model for prostatic stromal hyperplasia (ii) provides the advantage of enabling a test substance to be selected with more precise because the animal model is in a condition more similar to the clinical state (actual pathological state), and the advantage of more reliably selecting a clinically useful substance because the medicinal effects of the test substance can be observed and evaluated over a long period (3 weeks or more). Therefore, considering the advantages of the screening methods using these non-human animal models for prostatic stromal hyperplasia, it is preferable to conduct the aforementioned screening (first screening) using the non-human animal model for prostatic stromal hyperplasia (i) to roughly screen the test substances, and on the test substances selected thereby, the aforementioned screening (second screening) is conducted using the non-human animal model for prostatic stromal hyperplasia (ii). As a result, a clinically useful substance having a preventive effect on human prostatic stromal hyperplasia can be readily selected.

The substance thus selected is useful as an active ingredient in preventive agents for human benign prostatic hyperplasia, especially that accompanying stromal enlargement.

(2-2) Screening for a Substance Effective for Treating Human Benign Prostatic Hyperplasia Screening for a substance effective for treating benign prostatic hyperplasia can be practiced by administering a test substance into the non-human animal model for prostatic stromal hyperplasia (i) or (ii), rearing the animal model for a certain period, measuring the weight and histologic properties (stromal component ratio and the like) of the implanted tissue (fetal urogenital sinus-derived tissue) of the animal model, and evaluating the test substance.

As the non-human animal model for prostatic stromal hyperplasia (i) or (ii) used in screening for a therapeutic substance, among the non-human animal models for prostatic stromal hyperplasia described above, animal model (i) or (ii), which is produced by implanting a fetal urogenital sinus under the skin or beneath the prostatic capsule and rearing it for a certain period, is used. Desirably, animal model (i) or (ii) is used that is prepared by, implanting a fetal urogenital sinus, and then rearing it for 12 days or more, and preferably for 14 days or more, when it is a mouse or nude mouse; or implanting a fetal urogenital sinus, and then rearing it for 14 days or more, preferably for 21 days or more, when it is a rat or nude rat.

A method for administering a test substance into the non-human animal model for prostatic stromal hyperplasia (i) or (ii) is as described above. The non-human animal model for prostatic stromal hyperplasia (i) or (ii) administered with a test substance is reared for a certain period. Rearing conditions are not limited, and normal conditions and aseptic conditions can be employed as necessary. Examples of specific conditions are as those described in regard to the preventive substances above.

In this case, the rearing period after implantation is not limited, but the desirable rearing period is 12 days or more, and preferably 14 days or more, for any of a rat, a mouse, a nude rat, and a nude mouse. More specifically, 14 days or more of rearing period is desirable for a rat or nude rat, and especially 21 days or more. For a mouse or nude mouse, 12 days or more of rearing period is desirable, and especially 14 days or more.

After rearing, the test substance can be evaluated, after removing the implanted tissue (fetal urogenital sinus-derived tissue) from the model animal, by measuring the weight of the implanted tissue or examining the histological properties of the implanted tissue. Specifically, the test substance can be evaluated by measuring the weight of the implanted tissue (fetal urogenital sinus-derived tissue) and examining the weight reduction or the degree thereof, or by examining the reduction in the proportion of the stromal component (stromal area ratio) in the implanted tissue or the degree thereof. The proportion of the stromal component in tissue (stromal area ratio) can be calculated using, as described earlier, kera-tin staining, hematoxylin-eosin staining, or the like, although it is not limited to these methods.

In comparison with the weight of the implanted tissue (fetal urogenital sinus-derived tissue) or the proportion of the stromal component (stromal area ratio) of the implanted tissue of the non-human animal model for prostatic stromal hyperplasia before administering a test substance, a substance that reduces the weight of the implanted tissue (fetal urogenital sinus-derived tissue) or the proportion of the stromal component (stromal area ratio) of the implanted tissue can be identified as a substance that alleviates the enlargement of the prostate tissue or that reduces the enlarged prostate tissue, i.e., an active substance having a therapeutic effect on human prostatic stromal hyperplasia.

Specifically, a therapeutic substance can be selected as follows: A control non-human animal model for prostatic stromal hyperplasia administered with no test substances is reared in the same manner; the weight of the implanted tissue (fetal urogenital sinus-derived tissue) or the proportion of the stromal component (stromal area ratio) of the implanted tissue is measured; and the weight or the proportion of the stromal component (or extent of its increase) of the implanted tissue of the test animal administered with a test substance and the weight or the proportion of the stromal component of the implanted tissue of the aforementioned control animal are compared.

Such a therapeutic substance can be screened using as a test subject the non-human animal model for prostatic stromal hyperplasia either (i) or (ii). The respective screening methods and advantages thereof using the non-human animal model for prostatic stromal hyperplasia (i) or (ii) are as described above. Therefore, considering these advantages, it is preferable to conduct the aforementioned screening (first screening) using the non-human animal model for prostatic stromal hyperplasia (i) to roughly screen the test substances, and on the test substances selected thereby, the aforementioned screening (second screening) is conducted using the non-human animal model for prostatic stromal hyperplasia (ii). As a result, a clinically useful substance having a therapeutic effect on human prostatic stromal hyperplasia can be readily selected.

The substance thus selected is useful as an active ingredient in therapeutic agents for human benign prostatic hyperplasia, especially that accompanying stromal enlargement.

As required, the substance effective for preventing or treating human benign prostatic hyperplasia selected according to the screening method of the invention can be further subjected to additional efficacy tests, safety tests, clinical tests using human benign prostatic hyperplasia patients, or other such tests, to be screened as a highly effective and highly practical preventive or therapeutic substance.

The preventive or therapeutic substance thus screened can be industrially produced by chemical synthesis, biochemical synthesis (fermentation), or genetic engineering based on its structural analysis.

(3) Pharmaceutical Composition for Preventing or Treating Human Benign Prostatic Hyperplasia A substance effective for preventing or treating human benign prostatic hyperplasia obtained according to the aforementioned screening method can be prepared as a pharmaceutical composition per se, or it can be prepared as a pharmaceutical composition in combination with known a pharmaceutically acceptable carrier (including excipients, extenders, binders, lubricants, and the like) and a standard additive.

The present invention provides such pharmaceutical composition for preventing or treating human benign prostatic hyperplasia. The active ingredient of the pharmaceutical composition is not limited to those screened and directly obtained by the aforementioned methods, and include one chemically synthesized, biochemically synthesized, or genetically engineered according to standard methods based on data obtained from the above-screened substance.

The pharmaceutical composition can be orally or parenterally administered according to the form of the pharmaceutical composition prepared (tablet, pill, capsule, powder, granule, syrup, injection solution, drip fluid, externally-applied preparation, suppository, etc.). Although dosage cannot be specified because it depends on the type of active ingredient, administration route, administration subject, symptom, etc., it is about 0.0001 to about 5 g per day in single or divided doses.

The pharmaceutical composition can be effectively used as a preventive or therapeutic agent for human prostatic stromal hyperplasia caused by prostatic stromal enlargement, in particular.

(4) Method for Evaluating the Preventive or Therapeutic Effect of Test Substances on Human Benign Prostatic Hyperplasia The aforementioned non-human animal model for prostatic stromal hyperplasia (i) or (ii) can be used as an animal model in evaluating the preventive or therapeutic effect of each test substance on human benign prostatic hyperplasia.

Accordingly, the invention provides a method for evaluating the preventive or therapeutic effect of the test substance on human benign prostatic hyperplasia through the use of the non-human animal model for prostatic stromal hyperplasia (i) or (ii) of the present invention.

Specifically, such an evaluation method can be practiced by administering the test substance to the non-human animal model for prostatic stromal hyperplasia (i) or (ii), and measuring the preventive or therapeutic effect of the test substance administered on the implanted tissue (fetal urogenital sinuses or fetal urogenital sinus-derived tissue). In particular, the preventive or therapeutic effect of the test substance administered can be evaluated by examining its influence upon morphological changes, especially the proportion of the stromal component in the tissue (stromal area ratio), or weight of the implanted tissue (the fetal urogenital sinus or fetal urogenital sinus-derived tissue).

(4-1) Evaluation of Preventive Effect on Human Benign Prostatic Hyperplasia

The aforementioned non-human animal model for prostatic stromal hyperplasia (i) or (ii) used in the screening for a preventive substance can be likewise used in evaluating the preventive effect of the test substance. The method for administering the test substance to the non-human animal model for prostatic stromal hyperplasia (i) or (ii), and method for rearing it thereafter, are as described above in regard to the screening method.

After rearing, the preventive effect of the test substance can be evaluated, after removing the implanted tissue (fetal urogenital sinus-derived tissue) of the animal model, by measuring the weight of the implanted tissue or examining the histological properties of the implanted tissue, in a similar way as the screening method. Specifically, the preventive effect can be evaluated by measuring the weight of the implanted tissue (fetal urogenital sinus-derived tissue) and examining the influence upon weight increase, as specifically observed in prostate tissue affected by human benign prostatic hyperplasia, or by examining the influence upon the increase of the proportion of the stromal component (stromal area ratio), as specifically observed in prostate tissue affected by human benign prostatic hyperplasia. More specifically, the evaluation can be conducted as follows: A control non-human animal model for prostatic stromal hyperplasia administered with no test substances is reared in the same manner; the weight of the implanted tissue (fetal urogenital sinus-derived tissue) or the proportion of the stromal component (stromal area ratio) of the implanted tissue is measured; and the weight or the stromal area ratio (or extent of its increase) of the implanted tissue of the test animal administered with the test substance and the weight or the stromal area ratio of the implanted tissue of the aforementioned control animal is compared. Particularly, when the weight or the stromal area ratio of the implanted tissue (fetal urogenital sinus-derived tissue) of the test animal is lower than the weight or the stromal area ratio of the implanted tissue (fetal urogenital sinus-derived tissue) of the control animal (or when the increase of weight or stromal area ratio of the implanted tissue isolated from the test animal is inhibited), the test substance administered into such a test animal can be identified as having a preventive effect on human prostatic stromal hyperplasia, and according to the extent of its reduction (or extent of increase being reduced) the preventive effect can be evaluated.

The evaluation of preventive effect can be conducted using the non-human animal model for prostatic stromal hyperplasia either (i) or (ii). Animal model (i) or (ii) can be suitably selected according to the purpose of evaluation in consideration of the respective advantages described above of using the non-human animal model for prostatic stromal hyperplasia (i) or (ii). For example, when the preventive effect is to be roughly evaluated in a short period of time, it is preferable to use the non-human animal model for prostatic stromal hyperplasia (i). When the preventive effect is to be evaluated with high reliability, it is preferable to use the non-human animal model for prostatic stromal hyperplasia (ii).

(4-2) Evaluation of Therapeutic Effect on Human Benign Prostatic Hyperplasia

The aforementioned non-human animal model for prostatic stromal hyperplasia (i) or (ii) used in the screening for a therapeutic substance can be likewise used in evaluating the therapeutic effect of the test substance. The method for administering the test substance to the non-human animal model for prostatic stromal hyperplasia (i) or (ii), and method for rearing it thereafter, are as described above in regard to the screening method.

After rearing, the therapeutic effect of the test substance can be evaluated, after removing the implanted tissue (fetal urogenital sinus-derived tissue) of the model animal, by measuring the weight of the implanted tissue or examining the histological properties of the implanted tissue, in a similar way as the screening method. Specifically, whether the test substance has a therapeutic effect on human prostatic stromal hyperplasia or not, or the extent of such a therapeutic effect, can be evaluated according to the presence or absence of a reduction in weight of the implanted tissue (fetal urogenital sinus-derived tissue) or in proportion of the stromal component (stromal area ratio) of the implanted tissue (fetal urogenital sinus-derived tissue), or the extent of such a reduction, in comparison with the weight of the implanted tissue (fetal urogenital sinus-derived tissue) or the proportion of the stromal component (stromal area ratio) of the implanted tissue of the non-human animal model for prostatic stromal hyperplasia before administering the test substance. More practically, the evaluation of therapeutic effect can be conducted as follows: A control non-human animal model for prostatic stromal hyperplasia administered with no test substances is reared in the same manner; the weight of the implanted tissue (fetal urogenital sinus-derived tissue) or the proportion of the stromal component (stromal area ratio) of the implanted tissue is measured; and the weight of the implanted tissue (fetal urogenital sinus-derived tissue) or proportion of the stromal component (stromal area ratio) of the implanted tissue of the test animal administered with the test substance and the weight or stromal area ratio of the implanted tissue of the aforementioned control animal are compared. When the weight of the implanted tissue (fetal urogenital sinus-derived tissue) or proportion of the stromal component (stromal area ratio) of the implanted tissue of the test animal is lower than the weight or stromal area ratio of the implanted tissue (fetal urogenital sinus-derived tissue) of the control animal, the test substance administered into such a test animal can be identified as having a therapeutic effect on human benign stromal prostatic hyperplasia, and according to the extent of its reduction, the therapeutic effect can be evaluated.

Evaluation of therapeutic effect can be conducted using the non-human animal model for prostatic stromal hyperplasia either (i) or (ii). Animal model (i) or (ii) can be suitably selected according to the purpose of evaluation in consideration of the respective advantages described above of using the non-human the animal model for prostatic stromal hyperplasia (i) or (ii). For example, when the therapeutic effect is to be roughly evaluated in a short period of time, it is preferable to use the non-human animal model for prostatic stromal hyperplasia (i). When the therapeutic effect is to be evaluated with high reliability, it is preferable to use the non-human animal model for prostatic stromal hyperplasia (ii).

INDUSTRIAL APPLICABILITY

The animal model of the present invention exhibits a conspicuous increased prostate tissue weight, and has prostate-like tissue having stroma-dominant histological characteristics, as specifically observed in human benign prostatic hyperplasia patients. Herefrom, it can be considered as an animal model more closely reflecting the pathological conditions of human benign prostatic hyperplasia. Therefore, the animal model of the invention is useful in screening for pharmaceuticals that exhibit preventive or therapeutic effects on human benign prostatic hyperplasia, especially that accompanying stroma enlargement as its pathological condition, and in evaluating the medicinal properties of such pharmaceuticals. The present invention thus contributes to the development of pharmaceuticals to prevent or therapy human benign prostatic hyperplasia.

EXAMPLES

Examples are given below to illustrate the invention in more detail. While these examples provide embodiments of the invention, the scope of the invention is not limited to these examples.

Example 1

Production of Animal Model Having Prostate-like Stroma-Enlarged Tissue (1) Removal of Rat Fetal Urogenital Sinus Under ether anesthesia, fetuses were removed from female SD rats that were 21 days pregnant. From the removed male fetuses, urogenital sinuses were removed also under ether anesthesia while observing through a stereoscopic microscope. The urogenital sinuses were stored in a sterilized culture medium until implantation.

(2) Implantation Procedure

The abdominal skin adjacent the left femoral region of 6-week old BALB/c male nude mice was cut open about 2 to 3 mm under ether anesthesia. A single rat fetal urogenital sinus obtained in (1) above was subcutaneously implanted after incision using a forceps and the incision was sutured. Thereafter, these nude mice were reared in clean racks (Rat Bracket Cages, 3 to 4 mice/cage) for 2 weeks under the following conditions:

Temperature: 20 to 26° C.
Humidity: 30 to 70%
Lighting hours: 12-hour light-dark cycle; light-on at 8 am and light-out at 8 pm
Feed and feeding method: solid feed for mouse, MF (irradiated), ad libitum
Water and watering method: tap water, ad libitum (3) Weighing of Implanted Tissue (Rat Fetal Urogenital Sinus-derived Tissue)

Under ether anesthesia, the implanted tissues (rat fetal urogenital sinus-derived tissues) were removed from the above-described nude mice on 14 days after implantation, and the tissues were weighed. The results demonstrated that the weight of the implanted tissues (rat fetal urogenital sinus-derived tissues) on 14 days after implantation had increased about 9 to 10 times (to about 9 to 10 mg) compared with the weight before implantation (FIG. 1).

(4) Histological Evaluation of the Removed Implanted Tissue (Rat Fetal Urogenital Sinus-derived Tissue)

A paraffin block was produced by embedding and fixing the implanted tissues (rat fetal urogenital sinus-derived tissues) (14 days after implantation) in 10% neutral buffered formalin. This paraffin block was thin-sectioned and, according to the method described in (5) below, subjected to keratin staining, which specifically stains the epithelial tissue.

(5) Keratin Staining

The thin paraffin sections prepared above were keratin-stained according to the enzyme-labeled antibody technique (streptavidin method). In the enzyme-labeled antibody technique, an anti-keratin antibody (polyclonal rabbit anti-human keratin, Dako) was used as the primary antibody. Treatment after the reaction with the secondary antibody was conducted using a Histofine SAB-PO® kit (Nichirei).

Specifically, the thin paraffin sections obtained above were deparaffinized by xylol and subjected to digestion treatment by adding trypsin. These sections were then reacted with the primary antibody (anti-keratin antibody) and the secondary antibody (biotinylated anti-rabbit IgG (Goat), Nichirei), treated with peroxidase-conjugated streptavidin, and colored by 3,3'-diaminobenzidine. The nucleus was eventually ethylene blue-stained, and the stained specimens thus obtained were covered by a cover glass.

(6) Calculation of Stromal Area Ratio

Figure 2:
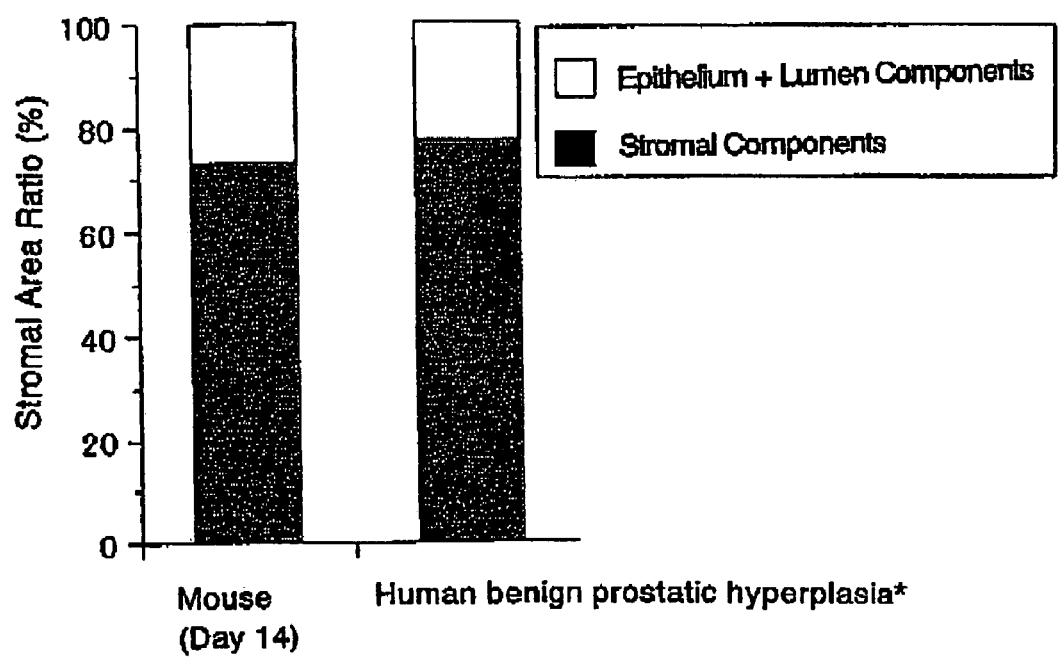
FIG. 2 shows a comparison of the stromal area ratio (%) of the tissue (tissue derived from the rat urogenital sinus) on 14 days after subcutaneous implantation into nude mice with the stromal area ratio (%) of the prostate tissue of human benign prostatic hyperplasia patients (Example 1 (6)).

Microscope images of the keratin-stained tissue sections were uploaded into a computer, and the stromal area ratio was calculated. Specifically, the stromal area was calculated as a difference (T−E) by subtracting the area (E) including the keratin-stained portions and the portions surrounded thereby (epithelium and lumen) from the area (T) of the entire tissue sections. The proportion of the stromal area (T−E) to the area (T) of the entire tissue section scalculated [(T−E)/(T)×100]

was regarded as the stromal area ratio (%) of the removed implanted tissue (rat fetal urogenital sinus-derived tissue). After implantation, the stromal area ratio in the implanted tissues was monitored over 28 days. The implanted tissues (rat fetal urogenital sinus-derived tissues) at least 14 days subsequent to implantation had a stromal area ratio of about 70%. This value nearly matched the stromal area ratio (%) of human benign prostatic hyperplasia patients (FIG. 2).

In the implanted tissue (rat fetal urogenital sinus-derived tissue), secreted substance was observed in the lumen composed of epithelial cells, thereby showing that the implanted rat fetal urogenital sinus was differentiated and developed into tissue (rat fetal urogenital sinus-derived tissue) having a secretory function equivalent to the prostate tissue.

Thereby, the inventors confirmed that the tissue (rat fetal urogenital sinus-derived tissue) implanted under the abdominal skin of the nude mouse formed histologically stroma-dominant, prostate-like tissue. A nude mouse produced according to the method described above can thus be considered as an animal model that has prostate-like, stroma-enlarged tissue histologically reflecting the pathological conditions of human benign prostatic hyperplasia, under the skin.

On 14 days after implantation, the weight of implanted tissues (rat fetal urogenital sinus-derived tissues) had increased about 10 times, as evidenced above, compared with the weight of rat fetal urogenital sinuses before implantation. Therefore, such a nude mouse, by using the change in configuration of tissue (stromal area ratio) or in weight of the implanted tissues (rat fetal urogenital sinus-derived tissues) as an indicator, can be effectively used in evaluating the medicinal effect of test pharmaceuticals (test substances) on benign prostatic hyperplasia.

Example 2

Production of Animal Model for Prostatic Stromal Hyperplasia (1) Removal of Rat Fetal Urogenital Sinus Under ether anesthesia, fetuses were removed from female SD rats that were 20 days pregnant. From the removed fetuses, the urogenital sinuses were removed under ether anesthesia while observing through a stereoscopic microscope. The urogenital sinuses were stored in a sterilized culture medium until implantation.

(2) Implantation Procedure

The prostate glands were exposed by midline incision using 6-week old male SD rats under ether anesthesia. The capsule of prostate right ventral lobe was slightly cut open while observing through a stereoscopic microscope. Two of the fetal urogenital sinuses obtained in (1) above were implanted using a forceps beneath the capsule, and the incision in the capsule was sutured. The cut abdominal skin then closed and the rats were reared for 2 to 8 weeks in normal rearing cages (Rat Bracket Cages, 3 to 4 rats/cage) under the following conditions:

Temperature: 20 to 26° C.
Humidity: 30 to 70%
Lighting hours: 12-hour light-dark cycle; light-on at 8 am and light-out at 8 pm
Feed and feeding method: solid feed for mouse, MF (irradiated), ad libitum
Water and watering method: tap water, ad libitum (3) Weighing of Implanted Tissue (Rat Fetal Urogenital Sinus-derived Tissue)

Figure 3:
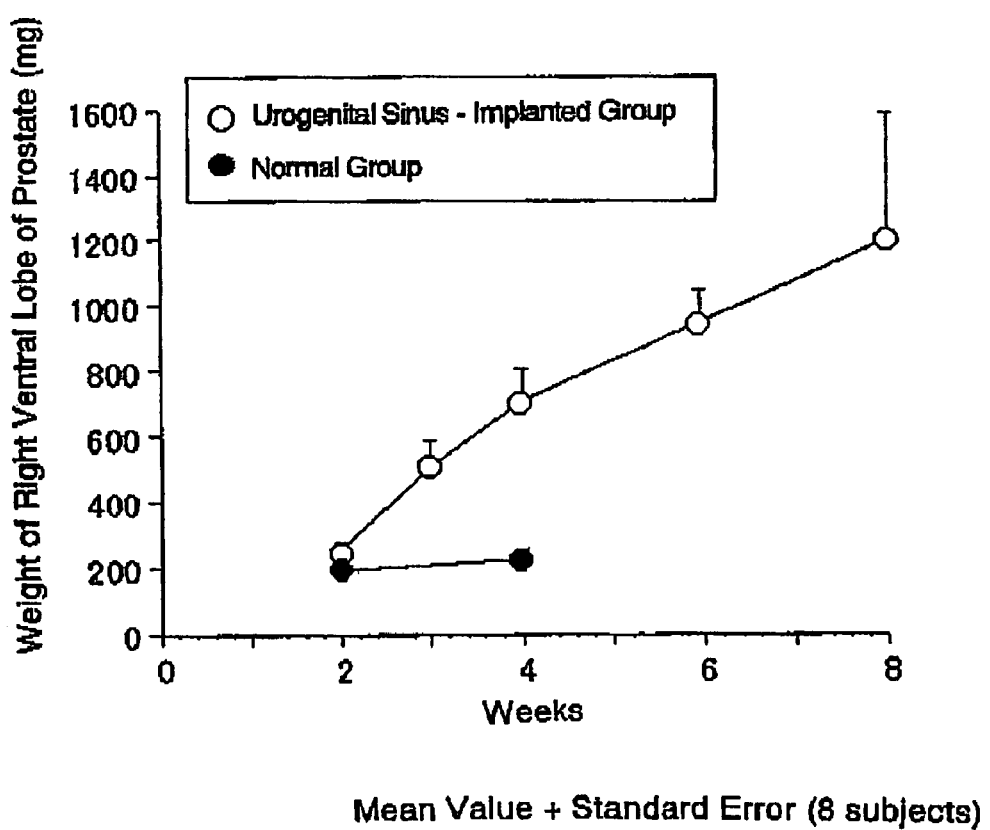
FIG. 3 shows the change in the weight of the prostate right ventral lobe of rat implanted with rat fetal urogenital sinus (Example 2 (3)). The each of -○- symbols represents the weight of the prostate right ventral lobe of rat (urogenital sinus-implanted group) implanted with rat urogenital sinuses (Example). The each of -●- symbols represents the weight of the prostate right ventral lobe of normal rat (normal group) with no implantation (Control Example).

Under ether anesthesia, the right ventral lobes (8 lobes×5) into which fetal urogenital sinuses had been implanted were removed from the above-described rats (n=8×5) on 2, 3, 4, 6, or 8 weeks after implantation, and were weighed. The results showed that the weight of the right ventral lobes exhibited a clear upward trend compared with the right ventral lobes of normal rats that were reared without having fetal urogenital sinuses implanted in them. The weight increase was specifically observed in the right ventral lobes removed after 3 weeks from implantation (on 3, 4, 6, or 8 weeks after implantation) (FIG. 3).

(4) Histological Evaluation of the Removed Implanted Tissue (Rat Fetal Urogenital Sinus-derived Tissue)

The implanted tissues (rat fetal urogenital sinus-derived tissues) obtained from the right ventral lobes removed on 2, 3, 4, 6, or 8 weeks after implantation were subjected to histological evaluation using the keratin staining in the same manners as in Example s 1 (4) and 1 (5).

(5) Calculation of Stromal Area Ratio

As in Example 1 (6), microscope image of the keratin-stained tissue sections was uploaded into a computer, and the stromal area ratio (%) of the implanted tissues (rat fetal urogenital sinus-derived tissues) was calculated.

Figure 4:
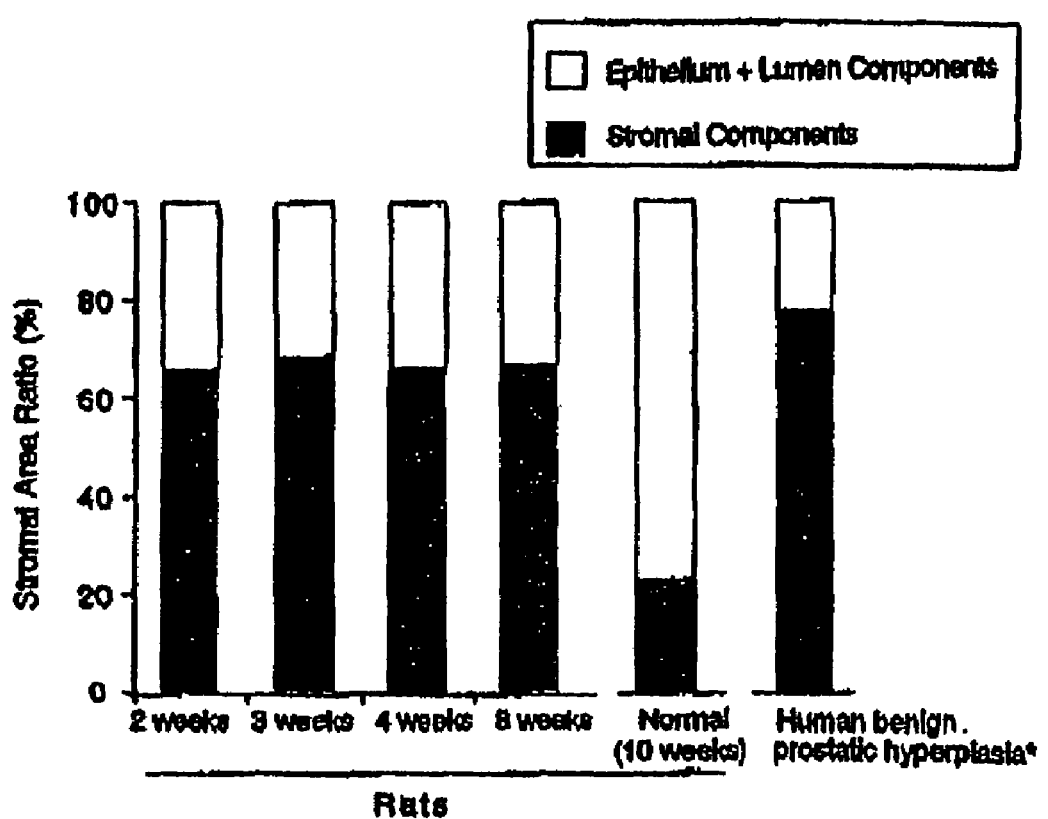
FIG. 4 shows a comparison of the stromal area ratio (%) of implanted tissue (rat urogenital sinus-derived tissue) removed on 2, 3, 4, or 8 weeks after implantation into the right ventral lobe of rat prostate gland with the stromal area ratio (%) of the prostate tissue of normal rat (10 weeks old) and the stromal area ratio (%) of the prostate tissue of human benign prostatic hyperplasia patient (Example 2 (5)).

The results demonstrated that implanted tissues (rat fetal urogenital sinus-derived tissues) at least 2 weeks subsequent to implantation had a stromal area ratio of about 70%. This value nearly matched the stromal area ratio (%) of human benign prostatic hyperplasia patients (FIG. 4). In contrast, the stromal area ratio (%) of the prostate tissue of normal rats (10 weeks old) was about 20%, and the tissue was epithelium-dominant.

In the implanted tissue (rat fetal urogenital sinus-derived tissues), secreted substance was observed in the lumen composed of epithelial cells, thereby showing that the implanted rat fetal urogenital sinus was differentiated and developed into tissue (rat fetal urogenital sinus-derived tissue) having a secretory function equivalent to prostate tissue.

Thereby, the inventors confirmed that the tissue (rat fetal urogenital sinus-derived tissue) implanted beneath the capsule of prostate right ventral lobe of the rats formed histologically stroma-dominant, prostate-like tissue. A rat produced according to the method described above can thus be considered as an animal model that has, beneath the prostatic capsule, prostate-like stroma-enlarged tissue histologically reflecting the pathological conditions of human benign prostatic hyperplasia.

As discusses above, the right ventral lobes of the prostate glands removed after 3 weeks from implantation (on 3, 4, 6, or 8 weeks after implantation) exhibited a marked increase in weight compared with the right ventral lobes before implantation, and the upward trend was significant compared to the right ventral lobes of the prostate glands of normal rats.

Therefore, such a rat, by using the change in configuration of tissue (stromal area ratio) or in weight of the implanted tissue (rat fetal urogenital sinus-derived tissue) as an indicator, can be effectively used in evaluating the medicinal effect of test pharmaceuticals (test substance) on benign prostatic hyperplasia.

Example 3

Production of Animal Model for Prostatic Stromal Hyperplasia (1) Removal of Rat Fetal Urogenital Sinus Urogenital sinuses were removed from the fetuses of female SD rats (donor animal) that were 20 days pregnant in the same manner as in Example 2 (1). The urogenital sinuses were stored in a sterilized culture medium until implantation.

(2) Implantation Procedure

In the same manner as in Example 2 (2), a single rat fetal urogenital sinus obtained in (1) above was implanted beneath the capsule of prostate right ventral lobe of each 6-week old male SD rat (recipient animal) (n=18×2), and the prostatic capsule was sutured. The implanted rats were reared in normal rearing cages for 3 to 6 weeks thereafter.

(3) Weighing of Implanted Tissue (Rat Fetal Urogenital Sinus-derived Tissue)

Figure 5:
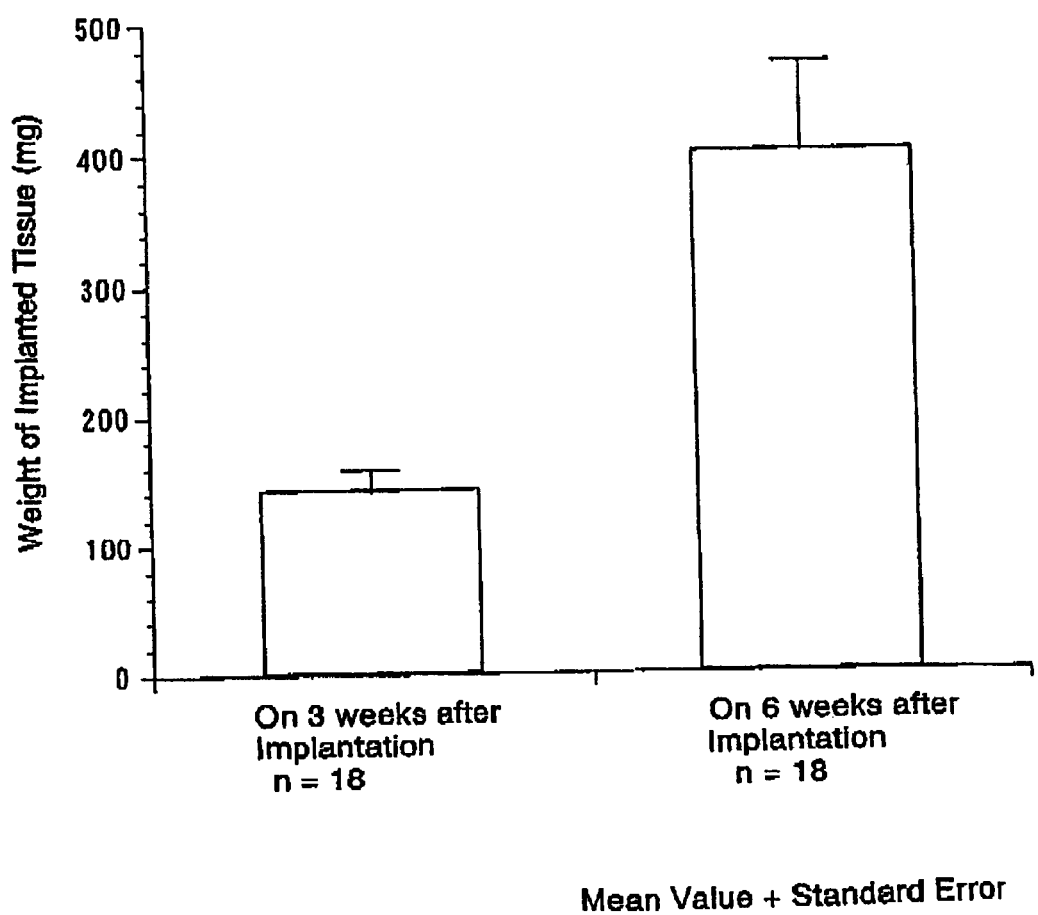
FIG. 5 shows the weight (mg) of implanted tissue (rat urogenital sinus-derived tissue) removed on 3 weeks or 6 weeks after implantation into the right ventral lobe of rat prostate gland (Example 3 (3)).

The implanted tissues (rat fetal urogenital sinus-derived tissues) were removed from the above-prepared rats under ether anesthesia on 3 weeks (n−18) and 6 weeks (n=18) after implantation, and were weighed. The results showed a significant weight increase in the implanted tissues (rat fetal urogenital sinus-derived tissues) after 3 weeks from implantation day (FIG. 5).

These results indicate that implanting a single fetal urogenital sinus beneath the capsule of prostate right ventral lobe can produce an animal model for prostatic stromal hyperplasia that histologically reflects the pathological conditions of human benign prostatic hyperplasia similar to Example 2 where two fetal urogenital sinuses were implanted.

Example 4

Animal models for prostatic stromal hyperplasia of the invention were prepared according to the methods described in Example 1 (1) and (2) by implanting the urogenital sinuses of rat fetuses (21 day-old) beneath the abdominal skin of 6-week-old male nude mice (BALB/cA Jcl-nu). For 2 weeks from the implantation day (day 0), a known therapeutic agent for benign prostatic hyperplasia, i.e., chlormadinone acetate (anti-androgen agent: 6-chloro-3,20-dioxopregna-4,6-dien-17,alpha-yl acetate; suspended or dissolved in 0.5% hydroxypropylmethyl cellulose (0.5% HPMC) solvent) was forcedly administered orally once a day (3 test substance-administered groups: 30 mg/kg·day, 100 mg/kg·day, 300 mg/kg·day; n=10 mice/group). Two weeks after the beginning of administration (day 14), the model animals were sacrificed by over anesthesia, and the implanted tissues (rat fetal urogenital sinus-derived tissues) were removed and weighed (weights from the test substance-administered groups). As a control experiment, for 2 weeks after implantation, model animals (solvent-administered group: n=10 mice) were forcedly administered with a solvent (0.5% HPMC), no chlormadinone acetate dissolved therein, once a day orally. Two weeks after the beginning of administration (day 14), the implanted tissues (rat fetal urogenital sinus-derived tissues) were likewise removed from the control mice and weighed (tissue weight from the solvent-administered group). The inhibition rate to weight increase of the subcutaneously-implanted, rat fetal urogenital sinus-derived tissues was calculated according to the formula shown in Equation 1, with respect to each chlormadinone acetate-administered group, and the effects of the therapeutic agent for benign prostatic hyperplasia (chlormadinone acetate) upon these tissues were then evaluated. Table 1 shows the results.

$$\left(1 - \frac{\text{Tissue weight from a test substance-administered group}}{\text{Tissue weight from the solvent-administered group}}\right) \times 100 \quad \text{(Equation 1)}$$

TABLE 1

| Amount administered | Rate of inhibition (%) |
|---|---|
| 30 mg/kg · day | 21.8 |
| 100 mg/kg · day | 39.5 |
| 300 mg/kg · day | 38.8 |

These results indicate that chlormadinone acetate, a known therapeutic agent for benign prostatic hyperplasia, acts on the fetal urogenital sinus-derived tissues subcutaneously developed during 2 weeks of rearing after implantation and significantly inhibits the tissues weight increase specifically observed in benign prostatic hyperplasia. These facts demonstrate that the animal model of the present invention having a fetal urogenital sinus-derived tissue under the skin can be used as an animal pathological model for evaluating therapeutic or preventive effects on benign prostatic hyperplasia.

Example 5

Animal models for prostatic stromal hyperplasia of the present invention were prepared according to the methods described in Examples 2 (1) and (2) by implanting the urogenital sinuses of rat fetuses (20 days of intrauterine life) beneath the capsules of prostate ventral lobes of 6-week-old male SD rats. The following Experiments (1) and (2) were conducted using these animal models for prostatic stromal hyperplasia:

Experiment (1): For 3 weeks from the implantation day (day 0), a known therapeutic agent for benign prostatic hyperplasia, i.e., chlormadinone acetate, suspended or dissolved in 0.5% HPMC solvent was forcedly administered once a day orally (test substance-administered group: 10 mg/kg·day; n=18 rats/group). Three weeks after the beginning of administration (day 21), the model animals were sacrificed by over anesthesia, and the implanted tissues (rat fetal urogenital sinus-derived tissues) were removed and weighed (tissue weight from the test substance-administered group). As a control experiment, for 3 weeks after implantation, model animals (solvent-administered group: n=18 rats) were forcedly administered with a solvent (0.5% HPMC) once a day orally, with no chlormadinone acetate dissolved therein. Three weeks after implantation (day 21), the implanted tissues (rat fetal urogenital sinus-derived tissues) were likewise removed from the control rats and weighed (tissue weight from the solvent-administered group). The rate inhibition to weight increase of the rat fetal urogenital sinus-derived tissues implanted beneath the prostatic capsules was calculated according to the formula shown in Equation 1 above, and the effects of the therapeutic agent on benign prostatic hyperplasia (chlormadinone acetate) were then evaluated.

Experiment (2): Animal models for prostatic stromal hyperplasia prepared as above were reared under the conditions described in Example 2 (2) for 3 weeks (until day 21) from the implantation day (day 0). The model animals of the control group (n=18) were then sacrificed by over anesthesia, and the implanted tissues (rat fetal urogenital sinus-derived tissues) were removed and weighed (tissue weight from the control group). In contrast, a known therapeutic agent for benign prostatic hyperplasia, i.e., chlormadinone acetate (prepared by being suspended or dissolved in 0.5% HPMC solvent), was forcedly administered once a day orally into the test substance-administered group (10 mg/kg, n=18) for a term of 3 weeks from 3 weeks after implantation (from day 21 to day 42). Three weeks after the start of administration (6 weeks after implantation, day 42), these model animals were sacrificed by over anesthesia, and the implanted tissues (rat fetal urogenital sinus-derived tissues) were removed and weighed (tissue weight from the test substance-administered group). Furthermore, as a control experiment, a solvent (0.5% HPMC), with no chlormadinone acetate dissolved therein, was forcedly administered orally into the solvent-administered group (n=18) for 3 weeks from 3 weeks after implantation. Three weeks after the start of administration (day 42), the implanted tissues (rat fetal urogenital sinus-derived tissues) were removed and weighed (tissue weight from the solvent-administered group). The rate inhibition to weight increase of the rat fetal urogenital sinus-derived tissues implanted beneath the prostatic capsules was calculated according to the formula shown below with respect to the test substance-administered group, and the effects of the therapeutic agent for benign prostatic hyperplasia (chlormadinone acetate) upon the tissues were then evaluated:

$$\left\{1 - \frac{\text{Tissue weight of the test substance-administered group} - \text{tissue weight from the control group}}{\text{Tissue weight of the solvent-administered group} - \text{tissue weight from the control group}}\right\} \times 100 \quad \text{(Equation 2)}$$

Table 2 shows the results of Experiments (1) and (2):

TABLE 2

| Period of administration | Amount administered | Rate of inhibition (%) |
|---|---|---|
| Ex. (1): for 3 weeks from implantation date | 10 mg/kg · day | 30.7 |
| Ex. (2): for 3 weeks from 3 weeks after implantation | 10 mg/kg · day | 67.0 |

These results indicate that chlormadinone acetate, a known therapeutic agent for benign prostatic hyperplasia, significantly inhibits the tissue weight increase as specifically observed in benign prostatic hyperplasia. This fact demonstrates that the animal model of the present invention produced by implanting a fetal urogenital sinus beneath the prostatic capsule can be used as an animal pathological model for evaluating therapeutic or preventive effects on benign prostatic hyperplasia.

The invention claimed is:

1. A mouse or rat model for prostatic stromal hyperplasia comprising a rat or mouse having an implanted fetal urogenital sinus from a donor mouse or rat implanted directly beneath the prostatic capsule, but not within the prostate gland, wherein said rat or mouse is genetically immunodeficient or is syngeneic to the mouse or rat from which the extraneous fetal urogenital sinus was obtained and wherein said mouse or rat exhibits prostatic stromal hyperplasia.

2. A method for producing a rat or mouse model for prostatic stromal hyperplasia comprising: implanting a fetal urogenital sinus of a male mouse or rat beneath the prostatic capsule of a mouse or rat that is syngeneic to the mouse or rat from which the urogenital sinus was obtained or beneath the prostatic capsule of genetically immunodeficient mouse or rat, wherein said implantation results in stroma-enlarged tissues under the prostatic capsule in said mouse or rat.

3. A method of screening a test substance for the treatment of benign prostatic stromal hyperplasia comprising:
    (i) administering a test substance to the rat or mouse model of prostatic stromal hyperplasia of claim 1; and
    (ii) measuring a change in the stromal area ratio or weight of the implanted extraneous urogenital sinus in comparison to a control rat or mouse model of prostatic stromal hyperplasia which was not administered said test substance, wherein a reduction in said stromal area ratio or weight of the implanted extraneous urogenital sinus when compared to said control rat or mouse model indicates that said test substance is a treatment for benign prostatic stromal hyperplasia.

* * * * *

UNITED STATES PATENT AND TRADEMARK OFFICE
CERTIFICATE OF CORRECTION

PATENT NO. : 7,417,175 B2 Page 1 of 1
APPLICATION NO. : 10/477077
DATED : August 26, 2008
INVENTOR(S) : Oda et al.

It is certified that error appears in the above-identified patent and that said Letters Patent is hereby corrected as shown below:

Title Pg, Item (73), please delete "Pharmaceuticals" and insert therefore,

--Pharmaceutical--.

Signed and Sealed this

Eleventh Day of November, 2008

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,417,175 B2 | |
| APPLICATION NO. | : 10/477077 | |
| DATED | : August 26, 2008 | |
| INVENTOR(S) | : Oda et al. | |

It is certified that error appears in the above-identified patent and that said Letters Patent is hereby corrected as shown below:

On the face page, right column at approximately line 23, please delete "incidene" and insert --incidence-- therefor.

At column 1, approximately line 30, please delete "lobes," and insert --lobes.-- therefor.

At column 2, approximately line 46, please delete "J E:," and insert --JE:-- therefor.

At column 2, approximately line 54, please delete "Implantation," and insert --implantation-- therefor.

At column 6, approximately line 33, please delete "Item" and insert --Items-- therefor.

At column 7, approximately line 27, please delete "E-2-3" and insert --F-2-3-- therefor.

At column 7, approximately line 34, please delete "below;" and insert --below:-- therefor.

At column 8, approximately line 36, please delete "Item" and insert --Items-- therefor.

At column 8, approximately line 39, please delete "With" and insert --with-- therefor.

UNITED STATES PATENT AND TRADEMARK OFFICE
CERTIFICATE OF CORRECTION

PATENT NO. : 7,417,175 B2
APPLICATION NO. : 10/477077
DATED : August 26, 2008
INVENTOR(S) : Oda et al.

It is certified that error appears in the above-identified patent and that said Letters Patent is hereby corrected as shown below:

At column 12, approximately line 9, please delete "dormant," and insert --dominant-- therefor.

At column 20, approximately line 21, after "libitum" please insert --.--.

At column 20, approximately line 67, please delete "section scalculated" and insert --sections calculated-- therefor.

At column 21, approximately line 67, after "libitum" please insert --.--.

Signed and Sealed this

Third Day of March, 2009

JOHN DOLL
*Acting Director of the United States Patent and Trademark Office*